United States Patent [19]
Sigler

[11] Patent Number: 5,722,537
[45] Date of Patent: Mar. 3, 1998

[54] DISINFECTANT CONTAINER FOR PACIFIER OR NIPPLE

[76] Inventor: Elizabeth Sigler, 29173 Tupelo Dr., Lacombe, La. 70445

[21] Appl. No.: 661,363

[22] Filed: Jun. 11, 1996

[51] Int. Cl.$^6$ ..................................................... B65D 55/00
[52] U.S. Cl. ........................... 206/205; 224/409; 422/300
[58] Field of Search ..................... 206/205, 210, 206/523; 224/409, 560, 561; 422/292, 294, 300

[56] References Cited

U.S. PATENT DOCUMENTS

| | | | |
|---|---|---|---|
| 2,323,615 | 7/1943 | Martineau | 206/16.6 |
| 3,021,002 | 2/1962 | Guyer | 206/494 |
| 3,321,068 | 5/1967 | Beach | 206/16.6 |
| 3,495,698 | 2/1970 | Draudt | 206/212 |
| 3,505,007 | 4/1970 | Green | 206/205 |
| 4,061,226 | 12/1977 | Essen | 206/306 |
| 4,428,497 | 1/1984 | Julius et al. | 206/210 |
| 4,462,507 | 7/1984 | Margulies | 206/210 |
| 4,620,579 | 11/1986 | Lowe et al. | 206/523 |
| 5,402,810 | 4/1995 | Donley | 206/205 |
| 5,584,386 | 12/1996 | Ahonen | 206/210 |

FOREIGN PATENT DOCUMENTS

| | | | |
|---|---|---|---|
| 460822 | 12/1950 | Italy | 422/300 |

*Primary Examiner*—Jimmy G. Foster
*Attorney, Agent, or Firm*—Joseph H. McGlynn; Patent & Trademark Services, Inc.

[57] ABSTRACT

A portable disinfectant container for an infant pacifier or infant nursing nipple, consisting of a half-oval shaped disinfectant container which is provided with a sponge that may be saturated with any appropriate non-toxic disinfectant solution. The disinfectant container is constructed of durable ABS plastic and has an attached hook for hanging on a purse, baby bag, stroller, or crib. The hinged lid of the disinfectant container may be flipped open and a pacifier or nipple inserted into a slit in the sponge for disinfectant purposes, the absorption qualities of the sponge preventing any type of spillage of the disinfectant.

11 Claims, 1 Drawing Sheet

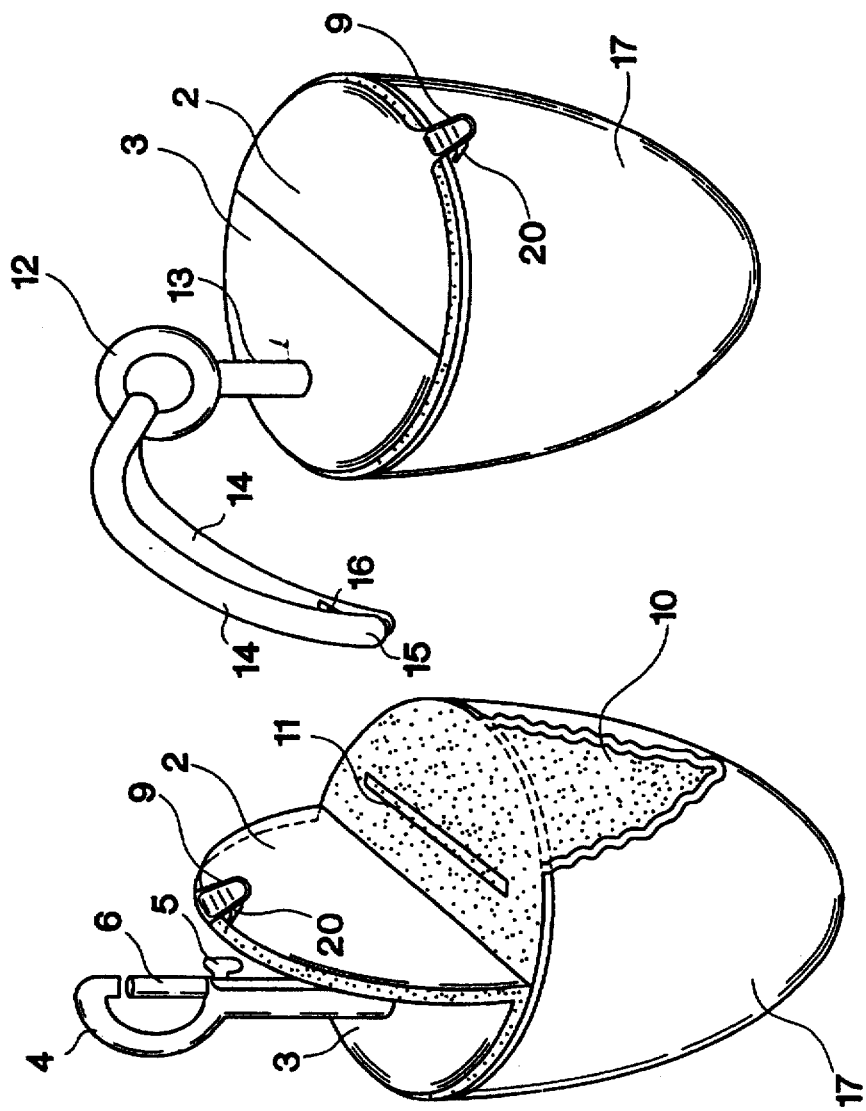
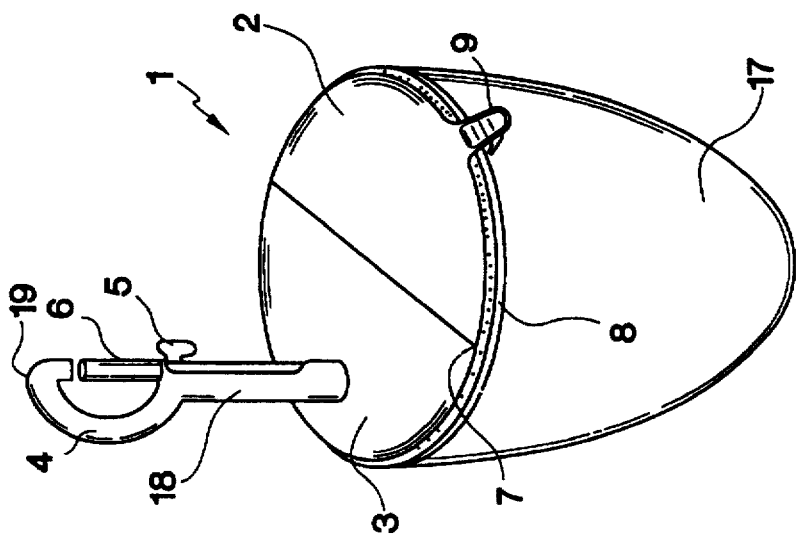

1

DISINFECTANT CONTAINER FOR PACIFIER OR NIPPLE

BACKGROUND OF THE INVENTION

This invention relates, in general, to a portable disinfectant container and, in particular, to a portable disinfectant container for disinfecting an infant pacifier or nursing bottle nipple.

The instant invention makes it possible to sanitize an infant pacifier or a nursing bottle nipple at any time or any place when an infant has dropped a pacifier or nursing bottle on the ground. This device is designed to allow for easy attachment to a purse, child's crib, child's stroller or baby bag; for ease of filling with sanitizing liquid; and for quick, easy usage when a pacifier or nursing bottle needs sanitizing. In addition, The Pacitizer is made of durable high-impact ABS plastic.

DESCRIPTION OF THE PRIOR ART

There is no indication in the prior art of a portable disinfectant device for disinfecting an infant pacifier or infant nursing bottle.

U.S. Pat. No. 2,323,615 shows a device for the purpose of disinfecting a temperature thermometer. The thermometer is contained in a fountain pen shaped container with a wick in the bottom that connects to a disinfecting container filled with disinfecting liquid.

U.S. Pat. No. 3,321,068 is a cylindrical container filled with disinfecting liquid into which a temperature thermometer may be inserted. A means is provided to attach the container vertically only. This does not allow for portability.

U.S. Pat. No. 3,495,698 has a cylindrical container for a temperature thermometer that has a bracket which may be attached to a vertical surface or placed at an angle on a horizontal surface. The cylindrical container is filled with disinfecting liquid.

U.S. Pat. No. 4,061,226 is a triangular shaped thermometer disinfecting case in which the lower portion contains disinfecting liquid and a cushioning portion at the base of the holder to cushion the thermometer tip. The case fits into a wall holder with a triangular shaped slot for receiving the case.

All of the prior art references are similarly designed for sterilization of temperature thermometers only. The majority of the prior art requires the use of the disinfecting liquid to be in a liquid state when an article is being sterilized.

SUMMARY OF THE INVENTION

The present invention is designed to be used as an easy-to-carry means of disinfecting an infant pacifier or nursing bottle nipple. The Pacitizer consists of a half-oval shaped container constructed of a durable high-impact ABS plastic. The top of the container is provided with a stationary lid portion and a half-circle hinged lid having a catch with a spring hook mounted behind the lid, the lid being snugly fitted to the lower part of the container. A highly absorbent polyurethane sponge is shaped to fit inside the lower part of the container. The sponge is provided with a slit into which disinfecting liquid may be poured, with the absorption quality of the sponge maintaining the disinfecting liquid in a non-spillable state for ease of portability of The Pacitizer.

The Pacitizer is further provided with a spring-biased latch hook for hanging from a purse strap, baby carrying bag or other similar article.

In a second embodiment, the lid is provided with an eyelet-type hook to which is attached a strap with a larger type fastening means for attaching The Pacitizer to an infant crib rail, a stroller handle or other article having a larger diameter.

When an infant drops a pacifier or nursing bottle on the ground, the disinfecting container lid is opened, the pacifier or nipple is inserted into the center slit of the absorptive sponge, and the pacifier or nipple is moved in an up and down motion, a sideways motion, or a circular motion so as to have all surfaces of the pacifier or nipple come into contact with the disinfecting liquid which has been absorbed by the sponge.

BRIEF DESCRIPTION OF THE DRAWINGS

FIG. 1 illustrates The Pacitizer with the spring-biased hook attached and with the movable lid in the closed position.

FIG. 2 is a cutaway view of The Pacitizer showing the absorptive sponge with the slit and the half-circle shaped movable lid in the open position.

FIG. 3 is a view of another embodiment of the invention showing an alternative attaching means which is a part of the stationary lid portion.

DESCRIPTION OF THE PREFERRED EMBODIMENTS

Referring now to the drawings in greater detail, FIG. 1 shows the present invention 1. It consists of a container 17 which is substantially egg shaped. Although this is the preferred shape, it should be understood that other shapes may be used without departing from the scope of the invention. Secured to the top of the container 17 is a fixed, immovable lid portion 3 in the shape of a half circle. The lid portion 3 can be attached to the container 17 by any conventional means such as, but not limited to, molding or ultrasonic welding.

Attached to the lid portion 3 is another lid portion 2 which is attached by any conventional hinge 7 so lid portion 2 is movable with respect to lid portion 3, and to the container 17. Attached to the fixed lid 3 is a fastener 4 which is attached by any conventional means. The fastener 4 has a stem 18 and integrally fastened thereto is a curved hook portion 19 which forms a substantially C-shape. A finger-operated spring biased tab 5 is slidably moved upward and downward within stem 18, to open and close bar 6 of the spring biased fastener 4 when it is desired to attach The Pacitizer 1 to a purse, baby bag, stroller, crib, etc.

The movable lid 2 can be held in a closed position (as shown in FIG. 1) by a catch 9 on the lid which cooperates with a complimentary catch 20 affixed to the container 17. The structure of the catches 9, 20 can assume many different shapes, but any conventional catch which will hold the lid 2 in a closed position can be used without departing from the scope of the invention.

The container 17 is preferably made from durable, high impact ABS plastic, although other material can be used without departing from the scope of the invention. The fixed lid 3 can be molded with the container 17, or it can be made separately and attached to the container 17 later. The movable lid 2 can be hinged to the fixed lid by any conventional hinge structure including, but not limited to, a so called living hinge.

FIG. 2 is a cutaway view showing the half-circle hinged lid 2 in its opened position. Within the container 17 is an absorptive sponge 10 which is illustrated with a slit 11 being cut into the central area of the sponge 10 to receive a pacifier or nursing bottle nipple for sterilization. It should be noted that the shape of the opening or slit 11 is not critical, and the opening could be any shape which will allow a nipple or pacifier, or similar item to be pushed into the sponge 11 and sterilized.

The sponge 11 can be saturated with any type of sterilizing liquid which will perform the intended function of cleaning the item placed within the sponge.

FIG. 3 illustrates another embodiment of The Pacitizer 1 in which the spring biased hook 4 is replaced with an eyelet type fastener 12 which is attached to the stationary lid portion 3 by means of vertical post 13 which is secured to the lid 3 by any conventional means including, but not limited to, molding or gluing. To the eyelet type fastener 12 is attached a strap 14, which is made in two parts. The length of straps 14 are designed to be fasten around larger articles that the spring clip 4 will not attach to, such as a crib rail, stroller handle, or other large article. The two ends of the straps 14 are provided with a first connection means 15 which may be detachably connected to second connection means 16 in order to mount the container 17 to a support. Any type of attachable/detachable fastening means such as a heavy-duty snap or VELCRO type hook and loop fastener may be used to close the ends of the strap 14.

The primary components of the Pacitizer would be best manufactured using a plastic injection molding process. This plastic molding process utilizes heat softened plastic material which is forced under very high pressure into a metal cavity mold which is relatively cool. The inside cavity mold is comprised of two or more halves and is the same desired shape as the product to be formed. High pressure hydraulics are used to keep the mold components together during the actual injection phase of the molding process. The injected plastic is allowed to cool and harden. The hydraulics holding the multiple component cavity together are released, the halves of the mold separated and the solid formed plastic item is removed. This process can easily be automated and is capable of producing extremely detailed parts at a very cost effective price. I have chosen ABS plastic over PVC (polyvinyl chloride) since PVC plastic produces acids and gases which will degrade the injection mold cavity over time.

The sponge 10 can be manufactured in two ways. The first would be to use "off the shelf" foam and cut it into a shape closely resembling the container 17. A slot for receiving the nipple or pacifier could be hand cut into the sponge and the sponge installed in the container 17. The second method would provide a more molded appearance to the slot 11 and involves injection molding under low pressure a polyurethane foam. Polyurethane foam is a two part mix of chemicals which when brought together, begins to produce a foaming material. Once this material is allowed to completely cure (usually in a few minutes) a solid foam product is produced. The mixture is usually injected into a mold which provides a sculptured look to the product which is an exact duplicate of the mold the foam was injected into.

In use a parent or guardian would use the Pacitizer to clean and sterilize a pacifier or bottle nipple. In the event an infant drops his/her pacifier or bottle, the user would open the cap 2, dip the nipple inside the disinfectant-filled sponge 10, remove it and then replace the lid 2 to prevent the liquid from drying out. For added convenience the spring biased hook 4 would allow the container 17 to hang in a convenient place to be ready to use. The straps 14 of the alternative embodiment would allow the container to be mounted in areas where the hook 4 would not work or be inconvenient.

Although The Pacitizer and the method of using the same according to the present invention has been described in the foregoing specification with considerable detail, it is to be understood that modifications may be made to the invention which do not exceed the scope of the appended claims and modified forms of the present invention by others skilled in the art to which the invention pertains will be considered infringements of this invention when those modified forms fall within the claimed scope of this invention.

What I claim as my invention is:

1. A portable disinfectant apparatus for disinfecting pacifiers or bottle nipples in combination with a disinfectant in the apparatus, said apparatus comprising:

a container having a bottom, sides and at least a partially open top, said container having a first lid portion and a second lid portion, said first lid portion being immovably attached to said container to cover a portion of said open top, said second lid portion being attached to said first lid portion so it can be moved from a first position in which it covers a portion of said open top to a second position in which said top is uncovered, an absorbent means positioned within said container for holding said disinfectant, means for securing said second lid portion in a closed position.

2. The portable disinfectant apparatus as claimed in claim 1 wherein:

said absorbent means is a sponge.

and said disinfectant is a non-toxic disinfecting solution.

3. The portable disinfectant apparatus as claimed in claim 1 wherein:

said absorbent means has an opening into which a pacifier or nursing bottle nipple may be introduced in order to bring said pacifier or nursing bottle nipple into contact with said disinfectant means.

4. The portable disinfectant apparatus as claimed in claim 1 wherein said container has means for mounting said container on a support structure.

5. The portable disinfectant apparatus as claimed in claim 4 wherein said mounting means is a spring biased hook.

6. The portable disinfectant apparatus as claimed in claim 4 wherein said mounting means is a pair of straps, one end of each strap is attached to said container, and another end of each strap has means to connect said another end of said straps together.

7. The portable disinfectant apparatus as claimed in claim 6, wherein said means to connect said another end of said straps together is a hook and loop type fastening means for detachably connecting said strap to a support.

8. The portable disinfectant apparatus as claimed in claim 1 wherein:

said absorbent means is removable from said container.

9. A portable disinfectant apparatus for disinfecting pacifiers or bottle nipples in combination with a disinfectant in the apparatus, as claimed in claim 1, wherein said absorbent material is a sponge.

10. A portable disinfectant apparatus for disinfecting pacifiers or bottle nipples comprising:

a container having a bottom, sides and at least a partially open top, said container having a first lid portion and a second lid portion, said first lid portion being immovably attached to said container to cover a portion of said open top, said second lid portion being attached to said first lid portion so it can be moved from a first position in which it covers a portion of said open top to a second position in which said top is uncovered, an absorbent means positioned within said container for holding a disinfectant means, means for securing said second lid portion in a closed position, and wherein said absorbent means has an opening into which a pacifier or nursing bottle nipple may be introduced in order to bring said pacifier or nursing bottle nipple into contact with said disinfectant means, said second lid portion is hinged to said first lid portion to pivot upwardly with respect to said first lid portion, and wherein said absorbent means is a sponge.

11. A portable disinfectant apparatus for disinfecting pacifiers or bottle nipples comprising:

a container having a bottom, sides and at least a partially open top, said container having a first lid portion and a second lid portion, said first lid portion being immovably attached to said container to cover a portion of said open top, said second lid portion being attached to said first lid portion so it can be moved from a first position in which it covers a portion of said open top to a second position in which said top is uncovered, an absorbent means positioned within said container for holding a disinfectant means, means for securing said second lid portion in a closed position, and wherein said container has means for mounting said container on a support structure, and wherein said mounting means is a spring biased hook which extends upwardly from said first lid portion.

* * * * *